United States Patent

Barer et al.

[11] 4,075,007
[45] Feb. 21, 1978

[54] N-CHLORO-CHLOROACETAMIDES AS HERBICIDES

[75] Inventors: Sol J. Barer, Plainsborough; Richard F. Stockel, Bridgewater Township, Middlesex County, both of N.J.

[73] Assignee: National Patent Development Corporation, New York, N.Y.

[21] Appl. No.: 471,062

[22] Filed: May 17, 1974

Related U.S. Application Data

[63] Continuation-in-part of Ser. No. 450,461, March 12, 1974, abandoned.

[51] Int. Cl.² .............................................. A01N 9/20
[52] U.S. Cl. ...................................................... 71/118
[58] Field of Search ........................................... 71/118

[56] References Cited

U.S. PATENT DOCUMENTS 3,133,808  5/1964  Hamm .................................. 71/118

OTHER PUBLICATIONS

Hamm et al., J. Agricultural and Food Chemistry, vol. 5, No. 1, 1957, pp. 30–32.

*Primary Examiner*—Lewis Gotts
*Assistant Examiner*—Catherine L. Mills
*Attorney, Agent, or Firm*—Cushman, Darby & Cushman

[57] ABSTRACT

N-chloro chloroalkanamides or chloro hydrocarbyl substituted alkanamides of the formula

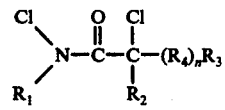

where $R_1$ is hydrogen or alkyl of 1 to 6 carbon atoms, $R_4$ is alkylene or chloroalkylene of 1 to 5 carbon atoms, $n$ is 0 or 1, $R_2$ and $R_3$ are hydrogen, chlorine, alkyl of 1 to 4 carbon atoms, alkaryl of up to 8 carbon atoms or aryl of up to 8 carbon atoms, have been found useful as herbicides. Preferably $n$ is 0 and $R_2$ and $R_3$ are hydrogen chlorine, phenyl or alkyl or 1 to 2 carbon atoms. Most preferably $R_2$ and $R_3$ are hydrogen or chlorine.

27 Claims, No Drawings

N-CHLORO-CHLOROACETAMIDES AS HERBICIDES

This application is a continuation-in-part of application Ser. No. 450,461 filed Mar. 12, 1974 and now abandoned.

The present invention relates to the use of N-chloro-chloroalkanamides or the like as herbicides.

German Pat. No. 616,381 discloses the preparation of N-chloro-haloacetamides.

The chemical reactivity of such compounds has been reported in *Tetrahedron Letters No.* 46, pages 4425–4428 (1971); *Rec. Trav. Chim.*, page 1093 et seq. (1930) and *J. Gen. Chem.* (*USSR*), Vol. 3, page 759 et seq. (1933).

Hamm in J. Agr. and Food Chem. Vol. 5, No. 1, pages 30–32 (1957) discloses that in regard to preemergence herbicidal activity alpha-chloroacetamide had no activity at 15 lbs/acre. alpha,alpha-dichloroacetamide had no activity at 25 lbs/acre, alpha, alpha, alpha-trichloroacetamide had no activity at 5 lbs/acre and fairly good activity at 15 lbs/acre, that N-lower alkyl and N,N-dilower alkyl alpha,alpha-dichloro and alpha,alpha,alpha-tri-chloroacetamides had no activity at 25 lbs/acre (or in one case at 5 lbs/acre) with the corresponding N-substituted alpha-chloro-acetamides had good activity at 5 lbs/acre, alpha chloro or beta chloro, or alpha,alpha dichloro, or alpha,beta dichloropropionamides as well as similar halo butyramides had no herbicidal activity at 25 lbs/acre.

Hamm U.S. Pat. No. 2,973,258 shows that alpha chloro N,N-dialkyl and the like are useful preemergent herbicides.

Speziale U.S. Pat. No. 2,864,682 and Hamm U.S. Pat. No. 2,863,752 show that N-phenyl alpha chloroacetamides have preemergent herbicidal activity.

Hamm U.S. Pat. No. 3,268,324 discloses that N-alkoxyalkyl alpha chloro acetamides are useful preemergent herbicides.

There has been no reported herbicidal activity for N-chloro-alpha-chloroacetamides or the like. It has now been found that N-chloro-alpha-chloro-amides of the formula

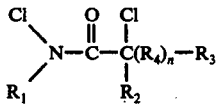

where $R_1$ is hydrogen or alkyl of 1 to 6 carbon atoms, $R_4$ is alkylene or chloroalkylene of 1 to 5 carbon atoms, $n$ is 0 or 1, $R_2$ and $R_3$ are hydrogen, chlorine alkyl of 1 to 4 carbon atoms, alkaryl of up to 8 carbon atoms or aryl of up to 8 carbon atoms have been found useful as both preemergent and post emergent herbicides. Preferably $n$ is 0 and $R_2$ and $R_3$ are hydrogen, chlorine, phenyl or alkyl of 1 to 2 carbon atoms. Most preferably $R_2$ is chlorine and $R_3$ is hydrogen or chlorine. $R_1$ is preferably hydrogen or alkyl of 1 to 4 carbon atoms. It is particularly surprising that compounds where $R_2$ and/or $R_3$ are chlorine have herbicidal activity in view of the lack of activity previously reported for the parent compounds which do not have an N-chloro substituent. The N-chloro alpha chloracetamide compounds also unexpectedly have superior herbicidal activity to the corresponding compounds devoid of the N-chloro substituent.

Illustrative of compounds useful in the invention include N-chloro alpha chloroacetamide,
N-chloro-alpha, alpha dichloroacetamide,
N-chloro-alpha,alpha,alpha trichloroacetamide,
N-chloro-N-methyl alpha,alpha,alpha trichloroacetamide,
N-chloro-N-hexyl alpha,alpha,alpha trichloroacetamide,
N-chloro-N-ethyl alpha,alpha,alpha-trichloroacetamide,
N-chloro-N-propyl alpha,alpha,alpha trichloroacetamide,
N-chloro-N-isopropyl alpha,alpha,alpha-trichloroacetamide,
N-chloro-N-butyl alpha,alpha,alpha-trichloroacetamide,
N-chloro-N-methyl alpha,alpha dichloroacetamide,
N-chloro-N-methyl alpha chloroacetamide,
N-chloro-N-ethyl alpha,alpha dichlroacetamide,
N-chloro alpha chloro propionamide,
N-chloro alpha,alpha dichloropropionamide,
N-chloro-N-methyl alpha chloropropionamide,
N-chloro alpha,beta dichloropropionamide,
N-chloro alpha chloro butyramide,
N-chloro alpha chloro valeramide,
N-chloro alpha chloro decamide,
N-chloro alpha chloro undecamide,
N-chloro alpha chloro alpha phenyl acetamide,
N-chloro alpha chloro alpha chloro alpha benzyl acetamide,
N-chloro alpha,alpha dichloro phenyl acetamide,
N-chloro alpha chloro alpha p-tolyl acetamide,
N-chloro alpha chloro alpha p-ethyl phenyl acetamide.

The products of the present invention can be used alone or they can be applied together with inert solids to form dusts, or can be suspended in a suitable liquid diluent, e.g., organic solvents or water.

There can also be added surface active agents or wetting agents and/or inert solids in the liquid formulations. In such case, the active ingredient can be from 0.01 to 95 percent by weight of the entire composition.

As organic solvents there can be employed hydrocarbons, e.g., benzene, toluene, xylene, kerosene, diesel fuel, fuel oil, and petroleum naphtha, ketones such as acetone, methyl ethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl carbitol acetate and glycerine, mixtures of water and organic solvents, either as solutions or emulsions, can be employed.

The novel products can also be applied as aerosols, e.g., by dispersing them in air by means of a compressed gas such as dichlorodifluoromethane or trichlorofluoromethane and other Freons and Genetrons, for example.

The products of the present invention can also be applied with adjuvants or carriers such as talc, pyrophyllite, synthetic fine silica, attapulgus clay, kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character. When a surface active agent is present it is usually employed in an amount of 0.05 - 1% by weight.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl) ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate, tertiary dodecyl polyethylene glycol thioether (Nonionic 218), long chain ethylene oxide-propylene oxide condensation products, e.g., Pluronic 61 (molecular weight 1000), polyethylene glycol ester of tall oil acids, sodium octyl phenoxyethoxyethyl sulfate, tris(polyoxyethylene) sorbitan monostearate (Tween 60), and sodium dihexyl sulfosuccinate.

The solid and liquid formulations can be prepared by any of the conventional procedures. For example, the compounds of the present invention can be applied to soil or growing plants to give herbicidal action.

The compounds can be applied at a rate of 0.5 to 100 lbs/acre, usually at 10 lbs/acre or less when they are strong herbicides, e.g., they can be used at 1 to 4 lbs/acre. In general they are applied to vegetation in a herbicidally effective amount.

The N-chloro compounds of the present invention can be prepared in conventional fashion by reacting the corresponding non-halogenated amides with an N-chlorinating agent such as an alkyl hypochlorite, e.g., methyl hypochlorite, ethyl hypochlorite, isopropyl hypochlorite, t-butyl hypochlorite and t-amyl hypochlorite or in the manner described in German Pat. No. 616,381. Any of the compounds employed in the invention can also be prepared by the method of Example 1 and 2 below.

Unless otherwise indicated all parts and percentages are by weight.

EXAMPLE 1

37 grams of chloroacetamide were added to 250 ml of methanol in a 500 ml flask. The mixture was cooled to +10° C and 50 ml of t-butyl hypochlorite were added and the mixture stirred for 1 hour. The green solution was stripped of solvent to recover N-chloro-alpha-chloroacetamide in 92% yield and 94% purity.

EXAMPLE 2

127 grams of dichloroacetamide $$(Cl_2CHC\underset{NH_2}{\overset{O}{\diagup\!\!\!\diagdown}})$$

were added to 500 ml of ethanol and 110 ml of t-butyl hypochlorite added dropwise. The solution was allowed to be stirred for one hour and then stripped of solvent under vacuum at room temperature. 160 grams of N-chloro-alpha,alpha-dichloroacetamide were obtained (99% yield) in 94% purity.

When trichloroacetamide is substituted in the above examples there is obtained N-chloro-alpha,alpha,alpha-trichloroacetamide (also called N-chloro-trichloroacetamide).

EXAMPLE 3

Method of Application as Herbicide

Plant Growing

Appropriate crop and weed species were seeded in individual 3 inch plastic pots. The seeds were covered with sand rather than soil to increase the sensitivity of preemergence testing (by reduced adsorption of chemicals on the soil). The soil depth was about 1.75 inches and the sand depth about 0.2 - 0.25 inches. For postemergence treatment the crop and weed species were seeded by growth-time requirement schedules and when the plants had reached suitable growth development, generally the first true leaf stage, individual pots were selected for uniformity. A total of 12 crops and weeds were used in primary evaluation. A sandy loam soil type was used.

Formulation of N-chlorotrichloroacetamide

N-chlorotrichloroacetamide was dissolved in methanol (100 grams/liter and diluted with water containing 1.0(v/v)% of N,N-Dimethylformamide, and NO % of (NONE) as wetting agents to obtain the indicated concentrations.

Application

The formulated N-chlorotrichloroacetamide was applied as a spray in a diluent volume of 50 gallons per acre. One carrying tray each of preemergence units and post-emergence units was passed through the sprayer on a conveyor belt at about 1.5 miles per hour. As the tray passed through the sprayer it tripped a microswitch which in turn activated a solenoid valve and released the spray treatment. The sprayer was normally equipped with a Teejet 8003E nozzle tip and was operated in the range of 45-90 p.s.i. pressure. Compressed air was used as a driving force to apply pressure to the spray chamber.

Holding and Observations

Immediately after treatment, the preemergence and postemergence units were moved to the greenhouse and held for observation and ratings. The preemergence units were watered-in with a gentle surface spray several minutes after spraying of the chemicals (a procedure shown to be effective in reducing loss of activity of volatile agricultural compounds such as trifluralin ($\alpha\lambda$,$\alpha$,$\alpha$-trifluoro-2,6-dinitro-N,N-dipropyl-p-toluidine) and EPTC (ethyl N,N-dipropyl-thiolcarbamate)).

Treated units were observed daily for interim response. Final observations were made approximately 14 days after postemergence treatment and 21 days after preemergence treatment.

Observations were reported as injury ratings, based

The herbicidal activity for this N-chloro compound is thus established, especially as a control for selected perennial weeds.

TABLE I

| HERBICIDE, PRE-EMERGENCE (INJURY RATING: PHYSIOLOGICAL RESPONSE)* | | | | | | | | | | | | |
|---|---|---|---|---|---|---|---|---|---|---|---|---|
| lb/A | YNSG(T) | WOAT | JMWD | VTLF | JNGS(S) | BDWD | MSTD | YLFX | BNGS | CBGS | CKBR | MNGY | Days |
| 4 | 10:R | 0:0 | 0:0 | 0:0 | 8:RD | 0:0 | 0:0 | 7:RD | 5:RD | 4:RD | 0:0 | 0:0 | 14 |
| 4 | 10:R | 0:0 | 0:0 | 2:R | 9:RDNe | 4:R | 0:0 | 7:RDNe | 3:RD | 2:RD | 0:0 | 0:0 | 21 |
| HERBICIDE, POST-EMERGENCE (INJURY RATING: PHYSIOLOGICAL RESPONSE)* | | | | | | | | | | | | |
| lb/A | YNSG(T) | WOAT | JMWD | VTLF | JNGS(S) | BDWD | MSTD | YLFX | BNGS | CBGS | CKBR | MNGY | DAYS |
| 4 | 0:0 | 0:0 | 0:0 | 0:0 | 0:0 | 8:R | 0:0 | 0:0 | 0:0 | 0:0 | 3:D | 0:0 | 14 |

*R = retarded/reduced
D = Distorted
Ne = Necrosis on a scale of zero to ten (0 – 10), zero indicating no injury and ten indicating complete control.

The following weeds and grasses were used in the tests:
Yellow nuts edge (YNSG)
Wild Oats (WOAT)
Jimsonweed (JMWD)
Velvetleaf (VTLF)
Johnsongrass (JNGS)
Bindweed (BDWD)
Mustard weed (MSTD)
Yellow Foxtail (YLFX)
Barnyard grass (BNGS)

N-chloro-N-propyl-alpha-chloroacetamide was tested for both pre-emergent and post emergent herbicidal activity in the same manner as N-chloro trichloroacetamide was tested. The activity was somewhat faster than Alachlor and appeared to be significantly faster in rate of development.

In post emergent application there resulted retardation and distortion of grasses and necrosis of broadleaf weeds. The post emergent activity was considerably superior to N-chloro-trichloroacetamide.

The results of the herbicidal testing with N-chloro-N-propyl-alpha-chloroacetamide are set forth in Table II below.

TABLE II (Compound 750)

| HERBICIDE, PRE-EMERGENCE (INJURY RATING: PHYSIOLOGICAL RESPONSE)* | | | | | | | | | | | | |
|---|---|---|---|---|---|---|---|---|---|---|---|---|
| lb/A | YNSG(T) | WOAT | JMWD | VTLF | JNGS(S) | BDWD | MSTD | YLFX | BNGS | CBGS | CKBR | MNGY | DAYS |
| 4 | 10:R | 9:RD | 0:0 | 0:0 | 2:RD | 0:0 | 4:RNe | 9:RD | 9:RD | 9:RD | 3:RD | 2:R | 14 |
| 4 | 10:R | 7:RD | 0:0 | 2:R | 4:RD | 3:R | 5:RNe | 8:RDNe | 6:RD | 9:RDNe | 3:RCl | 3:R | 21 |
| Reference Standard: Alachlor - Water Soluble Concentrate | | | | | | | | | | | | |
| 4 | 10:R | 9:RD | 2:R | 3:R | 8:RD | 8:RD | 7:R | 10:R | 10:R | 10:R | 3:R | 4:R | 14 |
| 4 | 10:R | 10:Ne | 3:R | 4:R | 7:RD | 8:R | 8:R | 9:RD | 10:R | 10:R | 4:R | 4:R | 21 |
| HERBICIDE, POST-EMERGENCE (INJURY RATING: PHYSIOLOGICAL RESPONSE) | | | | | | | | | | | | |
| lb/A | YNSG(T) | WOAT | JMWD | VTLF | JNGS(S) | BDWD | MSTD | YLFX | BNGS | CBGS | CKBR | MNGY | DAYS |
| 4 | 4:RDNe | 2:NeD | 9:NeCl | 5:Ne | 3:NeD | 2:Ne | 9:NeCl | 7:NeD | 3:NeR | 4:NeRD | 5:NeR | 8:NeCl | 6 |
| 4 | 7:RDNe | 5:RDNe | 10:Ne | 3:NeD | 6:RDNe | 3:NE | 10:Ne | 8:RDNe | 7:RDNe | 7:RDNe | 4:NeR | 9:Ne | 14 |
| Reference Standard: Alachlor - Water Soluble Concentrate | | | | | | | | | | | | |
| 4 | 1:D | 3:RD | 0:0 | 1:Ne | 2:NeD | 0:0 | 3:Ne | 5:NeD | 4:NeD | 3:NeD | 0:0 | 2:Ne | 6 |
| 4 | 7:RDNe | 6:RDNe | 9:RDNe | 1:NeD | 6:RDNe | 0:0 | 2:Ne | 8:RDNe | 8:RDNe | 7:RDNe | 2:R | 2:Ne | 14 |

Crabgrass (CBGS)
Cocklebur (CKBR)
Morning glory (MNGY)

Summary of Results

By preemergence application at 4 lb/acre N-chlorotrichloroacetamide induced activity 14 days after treatment very similar to that of Alachlor (2-chloro-2', 6'-diethyl-N-(methoxymethyl)acetanilide), typified by distortion with twisting and curling of leaves and grasses. N-chloro-trichloroacetamide was significantly effective on yellow nutsedge and Johnson grass from seed with lesser activity on yellow foxtail, barnyard grass and crabgrass. At 21 days after treatment the activity was holding on yellow nutsedge, Johnsongrass and yellow foxtail but was decreasing on barnyard grass and crabgrass.

By postemergence application at 4 lb/A, N-chloro trichloro-acetamide induced marked retardation (8 on a 0–10 scale) of bindweed and slight distortion of cocklebur.

What is claimed is:

1. A process for destroying undesired vegetation comprising treating the growing medium containing the vegetation with a herbicidally effective amount of an N-chloro compound of the formula

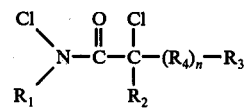

where $R_1$ is hydrogen or alkyl of 1 to 6 carbon atoms, $R_4$ is alkylene or chloroalkylene of 1 to 5 carbon atoms, $n$ is 0 or 1, $R_2$ and $R_3$ are hydrogen, chlorine, alkyl of 1 to 4 carbon atoms, aralkyl of up to 8 carbon atoms or aryl of up to 8 carbon atoms.

2. A process according to claim 1 wherein $n$ is 0, $R_2$ is hydrogen, chlorine, alkyl of 1 to 2 carbon atoms or phenyl, $R_3$ is hydrogen or chlorine, and $R_1$ is hydrogen or alkyl of 1 to 4 carbon atoms.

3. A process of inhibiting pre-emergent growth of unwanted vegetation which comprises treating the growing medium prior to emergence of the vegetation with a herbicidally effective amount of a compound having the formula set forth in claim 1.

4. A process according to claim 3 wherein $n$ is 0, $R_2$ is hydrogen, chlorine, alkyl of 1 to 2 carbon atoms or phenyl, $R_3$ is hydrogen or chlorine and $R_1$ is hydrogen or alkyl of 1 to 4 carbon atoms.

5. A process according to claim 4 wherein $R_2$ and $R_3$ are both chlorine.

6. A process according to claim 5 wherein $R_1$ is hydrogen.

7. A process according to claim 6 wherein the rate of application is not over 4 lbs/acre.

8. A process according to claim 4 wherein $R_2$ is chlorine and $R_3$ is hydrogen.

9. A process according to claim 8 wherein $R_1$ is hydrogen.

10. A process according to claim 4 wherein $R_2$ and $R_3$ are hydrogen.

11. A process according to claim 10 wherein $R_1$ is hydrogen.

12. A process according to claim 2 wherein the rate of application is not over 4 lbs/acre.

13. A process of inhibiting post-emergent growth of unwanted vegetation which comprises treating the growing medium and vegetation after emergence of the vegetation with a herbicidally effective amount of a compound having the formula set forth in claim 1.

14. A process according to claim 13 wherein $n$ is 0, $R_2$ is hydrogen, chlorine, alkyl of 1 to 2 carbon atoms or phenyl, $R_3$ is hydrogen or chlorine and $R_1$ is hydrogen or alkyl of 1 to 4 carbon atoms.

15. A process according to claim 14 wherein $R_2$ and $R_3$ are both chlorine.

16. A process according to claim 15 wherein $R_1$ is hydrogen.

17. A process according to claim 16 wherein the rate of application is not over 4 lbs/acre.

18. A process according to claim 14 wherein $R_2$ is chlorine and $R_3$ is hydrogen.

19. A process according to claim 18 wherein $R_1$ is hydrogen.

20. A process according to claim 14 wherein $R_2$ and $R_3$ are hydrogen.

21. A process according to claim 20 wherein $R_1$ is hydrogen.

22. A process according to claim 4 wherein $R_1$ is alkyl of 1 to 4 carbon atoms.

23. A process according to claim 22 wherein $R_2$ and $R_3$ are hydrogen.

24. A process according to claim 23 wherein the compound is N-chloro-N-propyl-alpha-chloroacetamide.

25. A process according to claim 14 wherein $R_1$ is alkyl of 1 to 4 carbon atoms.

26. A process according to claim 25 wherein $R_2$ and $R_3$ are hydrogen.

27. A process according to claim 26 wherein the compound is N-chloro-N-propyl-alpha-chloroacetamide.

* * * * *